United States Patent
Abrams et al.

(10) Patent No.: US 9,259,229 B2
(45) Date of Patent: Feb. 16, 2016

(54) SYSTEMS AND METHODS FOR ENCLOSING AN ANATOMICAL OPENING, INCLUDING COIL-TIPPED ANEURYSM DEVICES

(71) Applicant: Pulsar Vascular, Inc., San Jose, CA (US)

(72) Inventors: Robert M. Abrams, Los Gatos, CA (US); Chad Roue, San Jose, CA (US); Marc Jensen, San Jose, CA (US)

(73) Assignee: Pulsar Vascular, Inc., San Jose, CA (US)

( * ) Notice: Subject to any disclaimer, the term of this patent is extended or adjusted under 35 U.S.C. 154(b) by 183 days.

(21) Appl. No.: 13/831,280

(22) Filed: Mar. 14, 2013

(65) Prior Publication Data
US 2013/0304109 A1 Nov. 14, 2013

Related U.S. Application Data

(60) Provisional application No. 61/645,496, filed on May 10, 2012.

(51) Int. Cl.
*A61M 29/00* (2006.01)
*A61B 17/12* (2006.01)
*A61F 2/82* (2013.01)

(52) U.S. Cl.
CPC ..... *A61B 17/12145* (2013.01); *A61B 17/12113* (2013.01); *A61B 17/12172* (2013.01); *A61F 2002/823* (2013.01)

(58) Field of Classification Search
CPC .............. A61B 17/12145; A61B 17/1214; A61B 17/12113; A61B 17/12109; A61B 17/12118; A61F 2002/823
USPC ........................ 606/157, 158, 200, 213, 215
See application file for complete search history.

(56) References Cited

U.S. PATENT DOCUMENTS

| | | | |
|---|---|---|---|
| 3,868,956 A | 3/1975 | Alfidi et al. |
| 4,164,045 A | 8/1979 | Bokros et al. |
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |

(Continued)

FOREIGN PATENT DOCUMENTS

| AU | 2006304660 A1 | 4/2007 |
|---|---|---|
| CN | 1399530 A | 2/2003 |

(Continued)

OTHER PUBLICATIONS

Cordis NeuroVascular, Inc.; "Masstransit Microcatheter," Product Prochure; No. 153-8383-3; Miami Lakes, FL, USA (2003).

(Continued)

*Primary Examiner* — Jonathan W Miles
(74) *Attorney, Agent, or Firm* — Perkins Coie LLP

(57) ABSTRACT

The present disclosure describes implantable therapeutic devices and methods for endovascular placement of devices at a target site, such as an opening at a neck of an aneurysm. In particular, selected embodiments of the present technology comprise a coil loop, or tip, on a portion of the implantable device. The coil tip can provide a soft and/or smooth interface with the aneurysm and can provide improved coverage of the neck of the aneurysm.

14 Claims, 3 Drawing Sheets

(56) References Cited

U.S. PATENT DOCUMENTS

| | | |
|---|---|---|
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A | 3/2000 | Abrams et al. |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,048 B1 | 2/2002 | Chin et al. |
| 6,375,668 B1 | 4/2002 | Gifford et al. |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,613,074 B1 | 9/2003 | Mitelberg et al. |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,322,960 B2 | 1/2008 | Yamamoto et al. |
| 7,343,856 B2 | 3/2008 | Blohdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,254 B2 | 2/2011 | Klint et al. |
| 8,075,585 B2 | 12/2011 | Lee et al. |
| 8,388,650 B2 | 3/2013 | Gerberding et al. |
| 2003/0057156 A1 | 3/2003 | Peterson et al. |
| 2003/0139802 A1 | 7/2003 | Wulfman et al. |
| 2003/0181922 A1 | 9/2003 | Alferness |
| 2003/0181942 A1 | 9/2003 | Sutton et al. |

(56) References Cited

U.S. PATENT DOCUMENTS

| | | |
|---|---|---|
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0167597 A1 | 8/2004 | Costantino et al. |
| 2004/0167602 A1 | 8/2004 | Fischell et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0096728 A1 | 5/2005 | Ramer |
| 2005/0177224 A1 | 8/2005 | Fogarty et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0106418 A1* | 5/2006 | Seibold et al. ............... 606/213 |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0270902 A1 | 11/2007 | Slazas et al. |
| 2008/0039930 A1 | 2/2008 | Jones et al. |
| 2008/0147100 A1 | 6/2008 | Wallace |
| 2008/0183143 A1 | 7/2008 | Palisis et al. |
| 2008/0221600 A1 | 9/2008 | Dieck et al. |
| 2008/0269774 A1 | 10/2008 | Garcia et al. |
| 2009/0306678 A1 | 12/2009 | Hardert et al. |
| 2010/0094335 A1 | 4/2010 | Gerberding et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |

FOREIGN PATENT DOCUMENTS

| | | |
|---|---|---|
| CN | 101489492 A | 7/2009 |
| CN | 102202585 A | 9/2011 |
| CN | 102762156 A | 10/2012 |
| CN | 103230290 A | 8/2013 |
| CN | 103381101 A | 11/2013 |
| CN | 103582460 A | 2/2014 |
| CN | 103607964 A | 2/2014 |
| DE | 102008028308 A1 | 4/2009 |
| EP | 0820726 A2 | 1/1998 |
| EP | 00996372 A1 | 5/2000 |
| EP | 1269935 A2 | 1/2003 |
| EP | 1527753 A2 | 5/2005 |
| EP | 1951129 A2 | 8/2008 |
| EP | 2326259 A1 | 6/2011 |
| EP | 2451363 A2 | 5/2012 |
| EP | 2713904 A1 | 4/2014 |
| EP | 2713905 A1 | 4/2014 |
| HK | 1134421 A1 | 3/2014 |
| JP | 2001286478 A | 10/2001 |
| JP | 2009512515 A | 3/2009 |
| JP | 2013226419 A | 11/2013 |
| KR | 20080081899 A | 9/2008 |
| WO | WO-9724978 A1 | 7/1997 |
| WO | WO-9726939 A1 | 7/1997 |
| WO | WO-9731672 A1 | 9/1997 |
| WO | WO-9823227 A1 | 6/1998 |
| WO | WO-9850102 A1 | 11/1998 |
| WO | WO-9905977 A1 | 2/1999 |
| WO | WO-9907294 A1 | 2/1999 |
| WO | WO-9915225 A1 | 4/1999 |
| WO | WO-0013593 A1 | 3/2000 |
| WO | WO-0130266 A1 | 5/2001 |
| WO | WO02/00139 | 1/2002 |
| WO | WO-0213899 A1 | 2/2002 |
| WO | WO-02071977 | 9/2002 |
| WO | WO-02078777 | 10/2002 |
| WO | WO-02087690 | 11/2002 |
| WO | WO-03059176 A2 | 7/2003 |
| WO | WO-03075793 A1 | 9/2003 |
| WO | WO-2004019790 A1 | 3/2004 |
| WO | WO-2004026149 A1 | 4/2004 |
| WO | WO-2004105599 A1 | 12/2004 |
| WO | WO-2005033409 A1 | 4/2005 |
| WO | WO-2005082279 A1 | 9/2005 |
| WO | WO-2006119422 A2 | 11/2006 |
| WO | WO-2007/047851 A2 | 4/2007 |
| WO | WO-2008/151204 A1 | 12/2008 |
| WO | WO-2010/028314 A1 | 3/2010 |
| WO | WO-2011029063 A2 | 3/2011 |
| WO | WO-2012167137 A1 | 12/2012 |
| WO | WO-2012167150 A1 | 12/2012 |
| WO | WO-2012167156 A1 | 12/2012 |
| WO | WO-2013052920 A1 | 4/2013 |

OTHER PUBLICATIONS

Cordis NeuroVascular, Inc.; "Prolwer Select Plus Microcatheter," Product Brochure; No. 154-9877-1; Miami Lakes, FL, USA (2003).

Cordis NeuroVascular, Inc.; "Prowler Select LP Microcatheter," Product Brochure; No. 155-5585; Miami Lakes, FL, USA (2004).

Cordis NeuroVascular, Inc.; "Rapid Transit Microcatheter," Product Brochure; No. 152-7369-2; Miami Lakes, FL, USA (2003).

Extended European Search Report, European Application No. 06826291.4, Nov. 19, 2009, 7 pages.

Gupta et al. SMST-2003: Proc. Intl. Conf. Shape Memory Superelastic Technol.; Pacific Grove, CA; p. 639; 2003.

International Search Report and Written Opinion for Application No. PCT/US2010/047908, Mail Date May 25, 2011.

International Search Report and Written Opinion for International Application No. PCT/US2009/056133, Mail Date Oct. 26, 2009, 11 pages.

International Search Report and Written Opinion for International Application No. PCT/US2010/047908, mailing date Mar. 15, 2012, 11 pages.

International Search Report and Written Opinion for International Application No. PCT/US2012/040552, mailing date Aug. 28, 2012, 14 pages.

International Search Report and Written Opinion for International Application PCT/US2012/040536, mailing date Oct. 15, 2012, 17 pages.

International Search Report and Written Opinion for International Application PCT/US2012/040558, mailing date Oct. 8, 2012, 17 pages.

International Search Report and Written Opinion for International Application PCT/US2012/059133, mailing date Mar. 11, 2013,15 pages.

International Search Report and Written Opinion for International Application PCT/US2013/031793, mailing date Jun. 26, 2013, 14 pages.

International Search Report for International Application No. PCT/US06/40907, Mail Date May 1, 2008, 2 pages.

Micrus Copr.; "Concourse 14 Microcatheter" Product Brochure; Sunnyvale ,CA, USA.

Polytetraflouroethylene Implants, DermNet NZ, Nov. 11, 2005, http://dermetnz.org/polytetrafluoroethylene.html.

Singapore Examination Report for Singapore Application No. 200802811-0, Mail Date Jul. 12, 2009, 7 pages.

* cited by examiner

SYSTEMS AND METHODS FOR ENCLOSING AN ANATOMICAL OPENING, INCLUDING COIL-TIPPED ANEURYSM DEVICES

CROSS-REFERENCE TO RELATED APPLICATION

The present application claims the benefit of and priority to U.S. Provisional Patent Application No. 61/645,496, filed May 10, 2012, which is incorporated herein by reference in its entirety. Further, components and features of embodiments disclosed in the application incorporated by reference may be combined with various components and features disclosed and claimed in the present application.

TECHNICAL FIELD

The present technology relates to implantable therapeutic devices and methods for endovascular placement of devices at a target site, such as an opening at a neck of an aneurysm. For example, selected embodiments of the present technology comprise coil-tipped aneurysm devices that can occlude the opening at the neck of the aneurysm and inhibit dislodgement of the device relative to the aneurysm.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. Surgical techniques for repairing septal defects are also highly invasive. The risks related to anesthesia, bleeding, and infection associated with these types of procedures are high, and tissue that is affected during the procedure may or may not survive and continue functioning.

Minimally invasive surgical techniques have been developed to place occlusive devices within or across an opening or cavity in the body, such as in the vasculature, spinal column, fallopian tubes, bile ducts, bronchial and other air passageways, and the like. In general, an implantable device is guided along a delivery catheter and through a distal opening of the catheter using a pusher or delivery wire to deploy the device at a target site in the vasculature. Once the occlusive device has been deployed at the target site, it is detached from the pusher mechanism without disturbing placement of the occlusive device or damaging surrounding structures.

Minimally invasive techniques are also highly desirable for treating aneurysms. In general, the minimally invasive therapeutic objective is to prevent material that collects or forms in the cavity from entering the bloodstream and to prevent blood from entering and collecting in the aneurysm. This is often accomplished by introducing various materials and devices into the aneurysm. One class of embolic agents includes injectable fluids or suspensions, such as microfibrillar collagen, various polymeric beads, and polyvinylalcohol foam. Polymeric agents may also be cross-linked to extend their stability at the vascular site. These agents are typically deposited at a target site in the vasculature using a catheter to form a solid space-filling mass. Although some of these agents provide for excellent short-term occlusion, many are thought to allow vessel recanalization due to their absorption into the blood. Other materials, such as hog hair and suspensions of metal particles, have also been proposed and used to promote occlusion of aneurysms. Polymer resins, such as cyanoacrylates, are also employed as injectable vaso-occlusive materials. These resins are typically mixed with a radiopaque contrast material or are made radiopaque by the addition of a tantalum powder. Accurate and timely placement of these mixtures is crucial and very difficult because it is difficult or impossible to control them once they have been placed in the blood flow.

Implantable vaso-occlusive metallic structures are also well known and commonly used. Many conventional vaso-occlusive devices have helical coils constructed from a shape memory material or noble metal that forms a desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils.

Techniques for delivering conventional metallic vaso-occlusive devices to a target site generally involve a delivery catheter and a detachment mechanism that detaches the devices, such as a coil, from a delivery mechanism after placement at the target site. For example, a microcatheter can be initially steered through the delivery catheter into or adjacent to the entrance of an aneurysm either with or without a steerable guidewire. If a guidewire is used, it is then withdrawn from the microcatheter lumen and replaced by the implantable vaso-occlusive coil. The vaso-occlusive coil is advanced through and out of the microcatheter and thus deposited within the aneurysm or other vessel abnormality. It is crucial to accurately implant such vaso-occlusive devices within the internal volume of a cavity and to maintain the device within the internal volume of the aneurysm. Migration or projection of a vaso-occlusive device from the cavity may interfere with blood flow or nearby physiological structures and poses a serious health risk.

In addition to the difficulties of delivering implantable occlusion devices, some types of aneurysms are challenging to treat because of structural features of the aneurysm or because of particularities of the site. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms.

In view of such challenges, implanting conventional embolic coils, other structures, or materials in the internal space of an aneurysm has not been an entirely satisfactory surgical approach. The placement procedure may be arduous and lengthy because it often requires implanting multiple devices, such as coils, serially in the internal space of the aneurysm. Higher risks of complication from such sources as anesthesia, bleeding, thromboembolic events, procedural stroke, and infection are associated with such longer procedures. Moreover, because placement of structures in the internal space of an aneurysm does not generally completely occlude the opening, recanalization of the original aneurysm may occur, and debris and occlusive material may escape from within the aneurysm to create a risk of stroke or vessel blockage. Blood may also flow into the aneurysm after the placement of embolic devices, which may increase the risks of complication and further enlargement of the aneurysm.

Despite the numerous conventional devices and systems available for implanting embolic materials in an aneurysm and for occluding physiological defects using minimally invasive techniques, these procedures remain risky and rarely restore the physiological structure to its normal, healthy condition. It is also challenging to position conventional implantable devices during deployment, prevent shifting or migration of such devices after deployment, and preserve blood flow in neighboring vessels following after deployment.

DETAILED DESCRIPTION

The present disclosure describes implantable therapeutic devices and methods for endovascular placement of devices at a target site, such as an opening at a neck of an aneurysm. In particular, selected embodiments of the present technology comprise a coil loop, or tip, on a portion of the implantable device. The coil tip can provide a soft and/or smooth interface with the aneurysm and can provide improved coverage of the neck of the aneurysm. The following description provides many specific details for a thorough understanding of, and enabling description for, embodiments of the disclosure. Well-known structures, systems, and methods often associated with such systems have not been shown or described in detail to avoid unnecessarily obscuring the description of the various embodiments of the disclosure. In addition, those of ordinary skill in the relevant art will understand that additional embodiments may be practiced without several of the details described below.

Figure 1A:
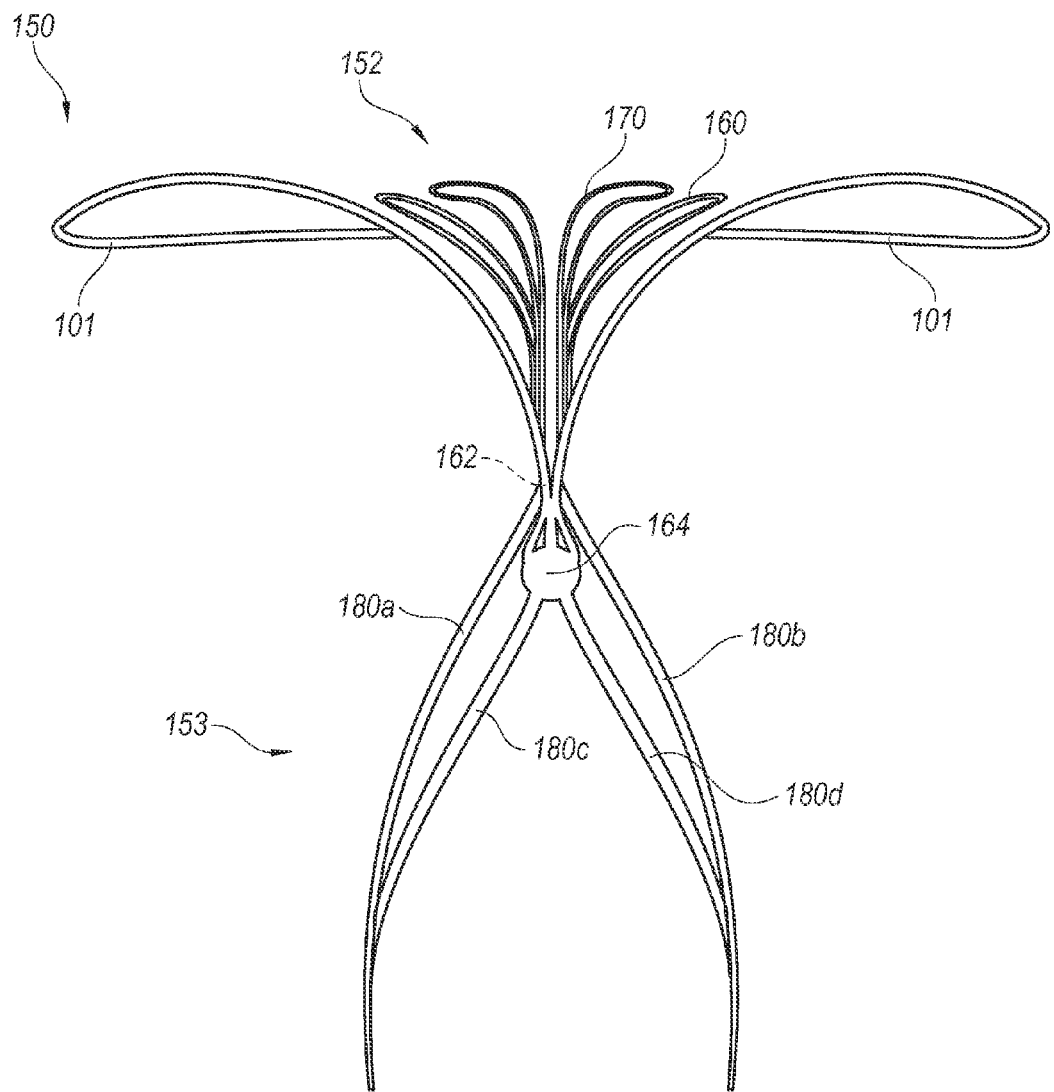
FIG. 1A is a front isometric view of an aneurysm device having coil tips configured in accordance with an embodiment of the technology.
Figure 1B:
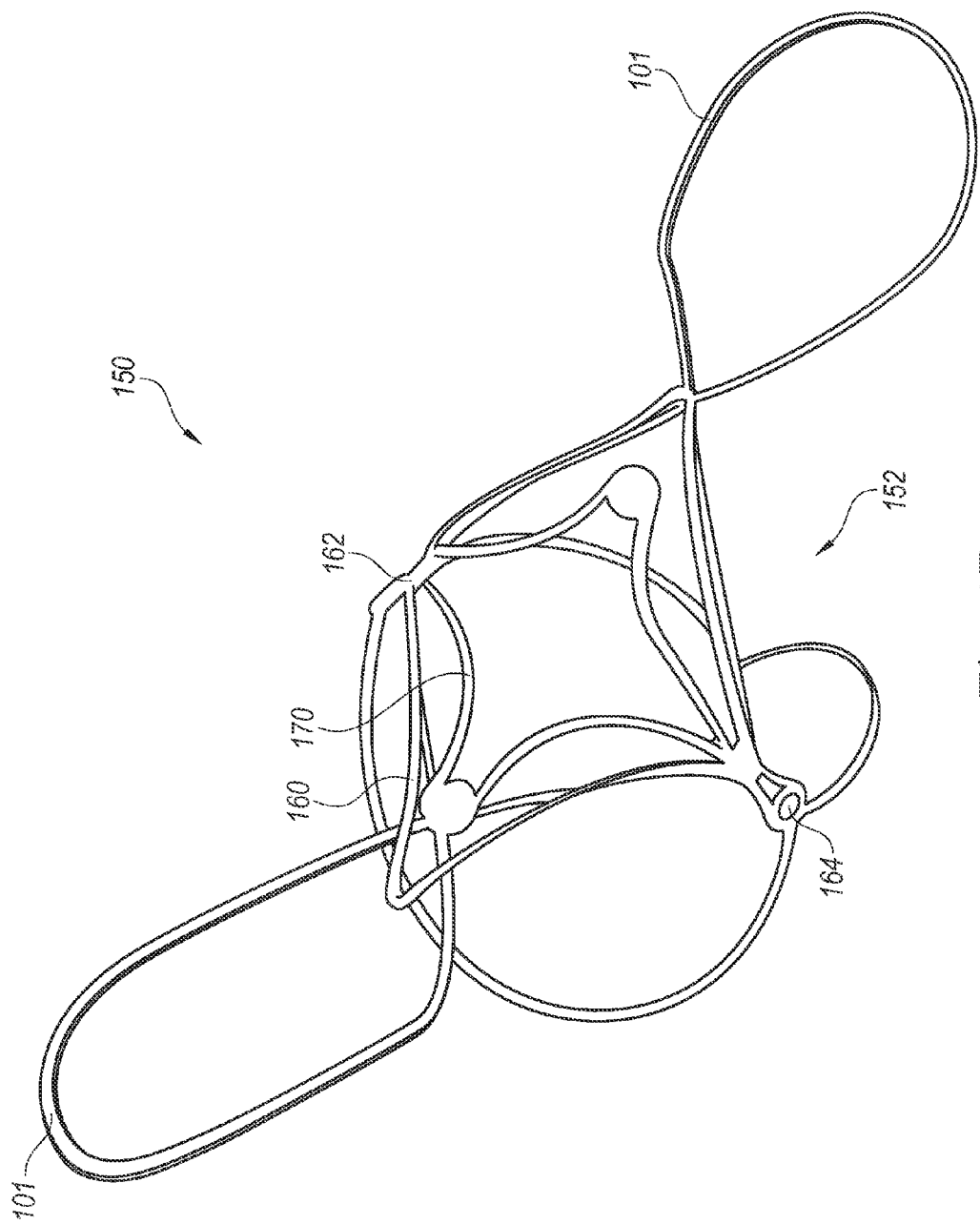
FIG. 1B is a top isometric view of the aneurysm device of FIG. 1A.

FIGS. 1A and 1B are views of an aneurysm device 150 having coil tips 101 configured in accordance with an embodiment of the technology. In particular, FIG. 1A is a front isometric view of the aneurysm device 150, and FIG. 1B is a top isometric view of the device 150. Referring to FIGS. 1A and 1B together, the aneurysm device 150 comprises a closure structure 152 having one or more coil tips or loops 101 (two are shown in the illustrated embodiment), and an optional supplemental stabilizer or support 153 extending from the closure structure 152. In further embodiments, the closure structure 152 may be employed without the supplemental stabilizer 153.

The closure structure 152 can be a frame, scaffold, or other structure that can at least partially occlude, span, or block the neck of an aneurysm to prevent embolic coils or other coagulative material within the aneurysm from escaping into the bloodstream. The proximally-extending sides of the closure structure 152 and the supplemental stabilizer 153 hold a curved portion of the closure structure 152 at the neck of the aneurysm. The closure structure 152 includes a perimeter support 160 and an inner support 170. The supports 160 and 170 can have a rhombus-like (e.g., diamond-shaped) shape or configuration. The perimeter support 160 and inner support 170 can be joined at junctions 162 and 164. The aneurysm device 150 can also have struts 180a-d projecting proximally from the junctions 162 and 164. Struts 180a-b are connected at junction 162 and struts 180c-d are connected at junction 164 to form the supplemental stabilizer 153 with proximal anchoring segments.

The coil tips 101 can be coupled to the closure structure 152 and/or the supplemental stabilizer 153. In the illustrated embodiment, for example, the coil tips 101 are coupled to the junctions 162 and 164 (e.g., by soldering or other attachment mechanism). In further embodiments, the coil tips 101 may be co-formed with the closure structure 152 and/or supplemental stabilizer 153. In several embodiments, the coil tips 101 extend peripherally and/or distally beyond the perimeter supports 160. In some embodiments, the coil tips 101 replace the perimeter supports 160. The coil tips 101 can comprise various biocompatible materials, such as biocompatible metal or plastic. In one particular embodiment, for example, the coil tips 101 comprise a platinum coil having a 0.005 inch outside diameter. In further embodiments, the coil tips 101 can comprise different materials or sizes. In several embodiments, the coil tips 101 can be a soft and/or smooth shape or material to easily interface with an aneurysm.

Figure 2:
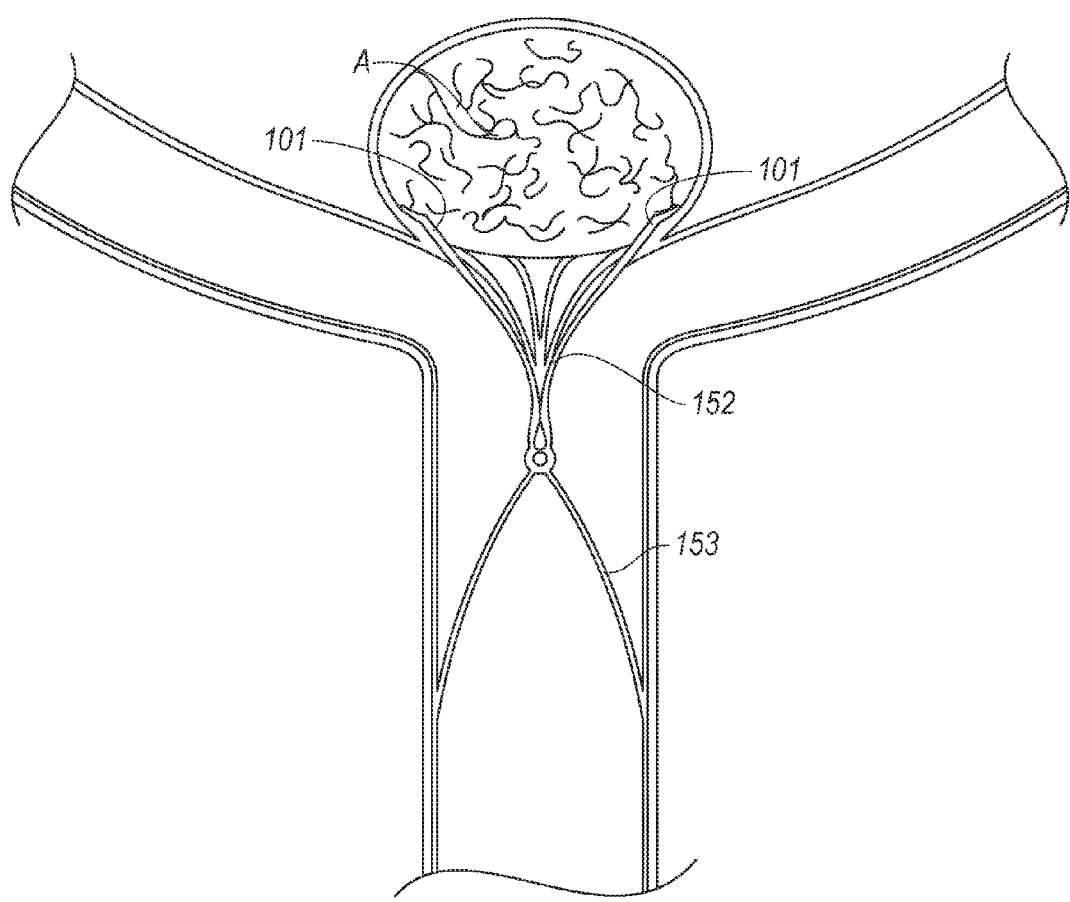
FIG. 2 is a front view of the aneurysm device of FIG. 1A implanted at an aneurysm and configured in accordance with embodiments of the technology.

While FIGS. 1A and 1B illustrate an embodiment wherein the coil tips 101 are in a generally "Figure 8" shape (having two "loops"), the coil tips 101 can take on alternate or additional 2-dimensional or 3-dimensional shapes in further embodiments. For example, the coil tips 101 can comprise one or more triangles, helices, spheres, complex basket shapes, or other atrial configurations. In some embodiments, the size and/or shape of the coil tips 101 can be tailored for improved neck coverage, improved anchoring ability, ease of delivery to a treatment site, or other feature. In other embodiments, there can be more or fewer coil tips 101 or portions of coil tips 101. In still further embodiments, a portion of the inner supports 170, perimeter supports 160, and/or coil tips 101 can be at least partially covered with a barrier configured to occlude at least a portion of the aneurysm In multiple device embodiments, the aneurysm device 150 is deployed such that it is anchored along a specific portion of an aneurysm neck. For example, FIG. 2 is a front view of the aneurysm device of FIG. 1A in a deployed configuration and implanted at an aneurysm A in accordance with embodiments of the technology. In the deployed configuration, the closure structure 152 has a distally projecting, arched framework portion. A proximal-facing aspect of the arch of the closure structure 152 extends laterally over the lumina of the bifurcating arteries. A distal-facing aspect of the arch of the closure structure 152 generally presses against the luminal surfaces of the bifurcating arteries. The distal-facing aspect of the closure structure 152 is configured to substantially align with or otherwise conform to the neck of the aneurysm by forming a curved surface that compatibly aligns with or engages the neck and the surrounding wall of the side branch vessels. In some embodiments, the distal-facing aspect has a complex curve, such as a hyperbolic paraboloid (e.g., a generally saddle-shaped form). In the illustrated embodiment, the hyperbolic paraboloid comprises a generally Y-shaped curve with a depressed central portion.

The coil tips 101 can extend distally and/or peripherally along or into the aneurysm and can improve the aneurysm device's ability to provide aneurysm neck coverage, as the coil tip 101 can be configured to be placed inside the aneurysm. For example, the coil tips 101 can be curved (e.g., complex curved) or parabolic shaped to better conform to the shape of the aneurysm or the vasculature to provide the desired degree of aneurysm occlusion and device stability. In the illustrated embodiment, the coil tips 101 can be placed within the aneurysm and can conform against the aneurysm wall, while the rest of the closure structure 152 (i.e., the inner supports 170 and perimeter supports 160) can conform against the luminal wall outside of the aneurysm. In some embodiments, the coil tips 101 contained in the aneurysm reside in the neck portion of the aneurysm and do not significantly or at all protrude past the neck portion into a body portion of the aneurysm. In still further embodiments, the coil tips 101 extend into the body of the aneurysm but do not conform to the aneurysm walls. In other embodiments, the coil tips 101 can conform against the luminal wall outside of the aneurysm.

The closure structure 152 can bridge a portion or all of the aneurysm neck and control blood flow into the aneurysm. In several embodiments, for example, the closure structure 152 spans unobtrusively over the lumina of the bifurcating arteries, forming no incursion into the vascular flow path. More particularly, the closure structure 152 can form a non-enclosed opening or hole, and in some embodiments can be entirely open in the proximal direction. In some embodiments, the coil tips 101 at least partially block or are positioned in the neck portion of the aneurysm A without causing significant stasis of flow in the aneurysm A.

The optional supplemental stabilizer 153 extends proximally from the closure structure 152 at an angle relative to a lateral axis. The supplemental stabilizer 153 can have struts that extend down into the parent artery and press outwardly against the luminal surface thereof. In further embodiments, the supplemental stabilizer 153 is absent.

EXAMPLES

The following Examples are illustrative of several embodiments of the present technology.

1. An aneurysm device endovascularly deliverable to a site proximate to an aneurysm in an artery, the aneurysm device comprising:
   a closure structure comprising a distal-facing aspect configured to at least partially span the aneurysm, and a proximal-facing aspect configured to arch over lumina of the artery; and
   a coil tip extending distally and/or peripherally from the closure structure and at least partially contained in the aneurysm.

2. The aneurysm device of example 1 wherein the coil tip comprises a loop shape, a basket shape, or a coil shape.

3. The aneurysm device of example 1 wherein the coil tip comprises platinum.

4. The aneurysm device of example 1, further comprising an attachment feature configured to couple the coil tip to the closure structure.

5. The aneurysm device of example 4 wherein the attachment feature comprises hardened solder.

6. The aneurysm device of example 1 wherein a portion of at least one of the closure structure or coil tip is at least partially covered with a barrier configured to occlude at least a portion of the aneurysm 7. The aneurysm device of example 1 wherein the coil tip resides in a neck portion of the aneurysm.

8. The aneurysm device of example 1 wherein the coil tip comprises a permeable framework configured to allow flow to or from the aneurysm.

9. The aneurysm device of example 1, further comprising a supplemental stabilizer proximally connected to the closure structure, wherein the supplemental stabilizer is configured to reside in the artery and press outward against a luminal wall thereof.

10. The aneurysm device of example 1 wherein the coil tip comprises a first coil tip, and wherein the device further comprises a second coil tip extending from the closure structure, and wherein the first coil tip and second coil tip extend peripherally from opposing lateral sides of the closure structure.

11. The aneurysm device of example 10 wherein the first coil tip and second coil tip each comprise a loop and together form a generally Figure-8 shape.

12. The aneurysm device of example 1 wherein the closure structure comprises a plurality of laterally opposing supports.

13. The aneurysm device of example 1 wherein at least one of the distal-facing aspect of the closure structure or the coil tip form a complex curved surface.

14. An aneurysm device endovascularly deliverable to a site proximate to an aneurysm, the aneurysm device comprising:
   a closure structure having a distal-facing aspect configured to at least partially occlude the aneurysm;
   a plurality of coil tips extending distally and/or peripherally from the closure structure and at least partially contained in the aneurysm; and
   a supplemental stabilizer connected to the closure structure, the supplemental stabilizer configured to reside in the artery and press outward against a luminal wall thereof.

15. The aneurysm device of example 14 wherein the coil tips each comprise a loop shape, a basket shape, or a coil shape.

16. The aneurysm device of example 14 wherein the coil tips reside in a neck portion of the aneurysm.

17. The aneurysm device of example 14 wherein the closure structure and coil tips comprise a permeable framework configured to allow flow to or from the aneurysm.

18. An aneurysm enclosure framework endovascularly deliverable to a site proximate to an aneurysm, the framework, when expanded at the site, comprising:
   a distal framework portion comprising a distal-facing aspect configured to at least partially enclose the aneurysm, and a proximal-facing aspect configured to arch over lumina of an artery; and
   a first coil tip distally extending in a first lateral direction relative to the distal framework portion and at least partially contained in the aneurysm; and
   a second coil tip distally extending in a second lateral direction opposite the first lateral direction and at least partially contained in the aneurysm.

19. The aneurysm device of example 18 wherein the first coil tip and second coil tip each comprise a loop and together form a generally Figure-8 shape.

20. The aneurysm device of example 18 wherein the first coil tip and second coil tip press or contour against at least one of a neck portion or wall portion of the aneurysm.

From the foregoing, it will be appreciated that specific embodiments of the disclosure have been described herein for purposes of illustration, but that various modifications may be made without deviating from the spirit and scope of the disclosure. For example, structures and/or processes described in the context of particular embodiments may be combined or eliminated in other embodiments. In particular, the aneurysm devices described above with reference to particular embodiments can include one or more additional features or components, or one or more of the features described above can be omitted. Further, the coil tips described herein may be employed with a variety of different aneurysm devices or assemblies in addition to those described above. Moreover, while advantages associated with certain embodiments of the disclosure have been described in the context of these embodiments, other embodiments may also exhibit such advantages, and not all embodiments need necessarily exhibit such advantages to fall within the scope of the disclosure.

We claim:

1. An aneurysm device endovascularly deliverable to a site proximate to an aneurysm in an artery, the aneurysm device comprising:
a closure structure comprising a distal-facing aspect configured to at least partially span the aneurysm, and a proximal-facing aspect configured to arch over lumina of the artery,
wherein the closure structure comprises a perimeter support including a plurality of struts and an inner support including a plurality of struts, and
wherein the inner support is within a boundary defined by the perimeter support;
a first coil tip extending from the closure structure and configured to be at least partially contained within the aneurysm; and
a second coil tip extending from the closure structure and configured to be at least partially contained within the aneurysm,
wherein the first and second coil tips extend peripherally from opposing lateral sides of the closure structure,
wherein a material of the first and the second coil tips is softer than a material of the closure structure, perimeter support, and inner support.

2. The aneurysm device of claim 1 wherein the first coil tip and the second coil tip each comprise a loop shape, a basket shape, or a coil shape.

3. The aneurysm device of claim 1 wherein the first and second coil tips comprise platinum.

4. The aneurysm device of claim 1, further comprising an attachment feature configured to couple the first and second coil tips to the closure structure.

5. The aneurysm device of claim 4 wherein the attachment feature comprises hardened solder.

6. The aneurysm device of claim 1 wherein a portion of at least one of the closure structure, the first coil tip, or the second coil tip is at least partially covered with a barrier configured to occlude at least a portion of the aneurysm.

7. The aneurysm device of claim 1 wherein at least one of the first coil tip and the second coil tip comprises a permeable framework configured to allow flow to or from the aneurysm.

8. The aneurysm device of claim 1, further comprising a supplemental stabilizer proximally connected to the closure structure, wherein the supplemental stabilizer is configured to reside in the artery and press outward against a luminal wall thereof.

9. The aneurysm device of claim 1 wherein the first coil tip and second coil tip each comprise a loop and together form a generally Figure-8 shape.

10. The aneurysm device of claim 1 wherein at least one of the distal-facing aspect of the closure structure, the first coil tip, or the second coil tip form a complex curved surface.

11. An aneurysm device endovascularly deliverable to a site proximate to an aneurysm, the aneurysm device comprising:
a closure structure having a distal-facing aspect configured to at least partially occlude the aneurysm;
wherein the closure structure comprises a perimeter support and an inner support, and wherein the inner support is within a boundary defined by the perimeter support;
a plurality of coil tips extending peripherally from the closure structure and configured to be at least partially contained in the aneurysm,
wherein the coil tips have a softer composition than that of the closure structure; and
a supplemental stabilizer connected to the closure structure, wherein the supplemental stabilizer is configured to reside in the artery and press outward against a luminal wall thereof.

12. The aneurysm device of claim 11 wherein the coil tips each comprise a loop shape, a basket shape, or a coil shape.

13. The aneurysm device of claim 11 wherein the coil tips reside in a neck portion of the aneurysm.

14. The aneurysm device of claim 11 wherein the closure structure and coil tips comprise a permeable framework configured to allow flow to or from the aneurysm.

* * * * *